US009220802B2

(12) United States Patent
Noel et al.

(10) Patent No.: US 9,220,802 B2
(45) Date of Patent: Dec. 29, 2015

(54) VEHICLE PHOTOCATALYTIC AIR PURIFICATION APPARATUS AND METHOD

(71) Applicants: Matthew W. Noel, Delmont, PA (US); Michael McKay, St. Thomas, VI (US)

(72) Inventors: Matthew W. Noel, Delmont, PA (US); Michael McKay, St. Thomas, VI (US)

(*) Notice: Subject to any disclaimer, the term of this patent is extended or adjusted under 35 U.S.C. 154(b) by 0 days.

(21) Appl. No.: 14/163,448

(22) Filed: Jan. 24, 2014

(65) Prior Publication Data

US 2015/0024176 A1  Jan. 22, 2015

Related U.S. Application Data

(60) Provisional application No. 61/756,658, filed on Jan. 25, 2013, provisional application No. 61/775,069, filed on Mar. 8, 2013.

(51) Int. Cl.
*B32B 3/00* (2006.01)
*A61L 9/20* (2006.01)
*B01J 21/00* (2006.01)
*B01J 35/00* (2006.01)

(52) U.S. Cl.
CPC ............... *A61L 9/205* (2013.01); *B01J 21/00* (2013.01); *B01J 35/004* (2013.01); *Y10T 428/24372* (2015.01)

(58) Field of Classification Search
CPC combination set(s) only.
See application file for complete search history.

(56) References Cited

U.S. PATENT DOCUMENTS

| 2010/0204037 A1* | 8/2010 | Gensler et al. ............... 502/159 |
| 2010/0297376 A1 | 11/2010 | Shi et al. |
| 2011/0293871 A1 | 12/2011 | Storfer-Isser |

OTHER PUBLICATIONS

"SkinWraps to Offer Permanon's Nano-Based UV Protection Spray to Vehicle Wrap Industry", Feb. 8, 2011, http://www.skinzwraps.com/.

* cited by examiner

*Primary Examiner* — Elizabeth Mulvaney
(74) *Attorney, Agent, or Firm* — The Webb Law Firm (57) ABSTRACT

Provided is a photocatalytic air purification vehicle wrap for at least partially covering an exterior surface of a vehicle. The vehicle wrap comprises a film or laminate material comprising a first surface area and a second surface area, the first surface area adapted to adhere to the exterior surface of the vehicle. The vehicle wrap further comprises a coating layer disposed on the second surface, the coating layer comprising a titanium dioxide solution cured onto the film or laminate material with ultraviolet radiation, wherein the coating layer is an outermost layer of the vehicle wrap such that the cured titanium dioxide solution is exposed to air surrounding the vehicle when the first surface area is adhered to the exterior surface of the vehicle.

20 Claims, 5 Drawing Sheets

VEHICLE PHOTOCATALYTIC AIR PURIFICATION APPARATUS AND METHOD

CROSS REFERENCE TO RELATED APPLICATIONS

This application claims benefit of priority from U.S. Provisional Patent Application No. 61/756,658, filed Jan. 25, 2013 and U.S. Provisional Patent Application No. 61/775,069, filed Mar. 8, 2013, which are incorporated herein by reference in their entirety.

BACKGROUND OF THE INVENTION

1. Field of the Invention

The present disclosure relates generally to air purification and, more specifically, to an apparatus and method for photocatalytic air purification using a vehicle.

2. Description of Related Art

In high-traffic areas, ground-level pollution created by vehicle exhaust contributes to smog and other air quality issues. Especially where vehicles wait for long periods of time in traffic, idling exhaust fumes affect air quality for everyone and particularly affect the health of commuters.

Titanium dioxide ($TiO_2$) is used for whitening items through white pigmentation and oxidizing harmful particles. When titanium dioxide is exposed to ultraviolet (UV) light, hydroxyl radicals and super-oxide ions are created. These reactive electrons combine and react with other elements in the air to effectively oxidize volatile organic compounds (VOCs), bacteria, and other harmful compounds.

Titanium dioxide is used in building materials, such as paneling and concrete, to make these materials easier to clean (e.g., by breaking down bacteria and other elements through photocatalysis), and to provide white pigmentation.

For at least the foregoing reasons, there is a need for an apparatus and method for photocatalytic air purification of ground-level pollutants using a vehicle.

SUMMARY OF THE INVENTION

Generally, the present invention provides methods and apparatuses for photocatalytic air purification using a vehicle that address or overcome certain drawbacks and deficiencies in known air purification methods and apparatuses.

According to a preferred and non-limiting embodiment, provided is a vehicle wrap for at least partially covering an exterior surface of a vehicle, comprising a film or laminate material comprising a first surface area and a second surface area, where the first surface area is adapted to adhere to the exterior surface of the vehicle. The vehicle wrap also includes a coating layer disposed on the second surface, the coating layer comprising a titanium dioxide solution cured onto the film or laminate material with ultraviolet radiation, wherein the coating layer is an outermost layer of the vehicle wrap such that the cured titanium dioxide solution is exposed to air surrounding the vehicle when the first surface area is adhered to the exterior surface of the vehicle.

According to another preferred and non-limiting embodiment, provided is a method for making a vehicle wrap, comprising the steps of: providing a vinyl material comprising a first surface and a second surface opposite the first surface, the first surface adapted to statically adhere to an exterior surface of a vehicle; printing at least one graphic or image on the second surface of the vinyl material; coating the second surface of the vinyl material with a liquid titanium dioxide solution using a coating machine; and curing the coated vinyl material with ultraviolet radiation.

According to a further preferred and non-limiting embodiment, provided is a vehicle wrap for at least partially covering an exterior surface of a vehicle, comprising at least a portion of a sheet of vinyl material comprising a first surface area and a second surface area opposite the first surface area, the first surface area adapted to removably adhere to the exterior surface of the vehicle, the second surface area comprising a coating of a titanium dioxide solution, wherein the coating on the second surface area is the outermost layer of the vehicle wrap and is exposed to air when the first surface area of the vehicle wrap is adhered to the exterior surface of the vehicle such that the coating produces a photocatalytic effect when the vehicle is exposed to air and sunlight.

According to another non-limiting embodiment, provided is a photocatalytic air purification device for an automobile that includes a material adapted to be magnetically attached to an exterior surface of the automobile. The material may include a magnetic contact surface and an exposed surface, and the exposed surface may comprise titanium dioxide. In some examples, the magnetic material of the photocatalytic air purification device may be substantially circular. The magnetic material may further comprise a thickness, and an area of the magnetic material may be least one thousand times larger than the thickness. In some non-limiting embodiments, the thickness may be less than one centimeter, and the area may be at least thirty-five square centimeters. Additionally, as an example, the exterior surface of the automobile may be a front hood of the automobile. Further, the material may further comprise at least one graphic visible on or through the exposed surface.

According to another preferred and non-limiting embodiment, provided is a method for purifying air using an automobile, comprising the steps of providing a flexible magnetic material having at least two surfaces, wherein at least one surface of the magnetic material comprises titanium dioxide; and affixing the pliable magnetic material to an exterior surface of an automobile. Further, in embodiments, the exterior surface may comprise a front hood of the automobile. In some embodiments, the magnetic material may be substantially circular.

According to another preferred and non-limiting embodiment, provided is a method for making an automobile air purifier, comprising the steps of providing a flexible magnetic material having an outer surface; and coating the outer surface with a material comprising titanium dioxide. The method, in embodiments, may further comprise applying the flexible magnetic material to an exterior surface of an automobile, such that the outer surface of the flexible magnetic material is exposed to air. Additionally, the exterior surface may include a front hood of the automobile. In some non-limiting embodiments, the flexible magnetic material may include a thickness, and the thickness may be at least one hundred times smaller than an area of the outer surface of the flexible magnetic material.

In a further non-limiting embodiment, provided is an air purification device comprising a mesh screen, the mesh screen comprising an outer rim and an inner area, wherein at least a portion of the inner area of the mesh screen comprises titanium dioxide; and at least one attachment means for attaching the mesh screen to a surface. The at least one attachment means may include at least one suction cup. Further, in examples, the at least one attachment means may comprise at least three suction cups spaced evenly along the outer rim of the mesh screen, and the inner area may comprise at least one square foot. Moreover, the at least one attachment means may include at least three suction cups spaced evenly along the outer rim of the mesh screen, and an area of the inner area may include at least one square foot.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE PREFERRED EMBODIMENTS

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

According to a preferred and non-limiting embodiment, provided is an air purification device in the form of a vehicle wrap that covers at least a portion of a vehicle such as, for example, a truck, car, van, bus, train, and/or other like vehicle. The vehicle wrap may include a film or laminate that adheres to the exterior of the vehicle using static, magnetism, adhesives, and/or the like. The vehicle wrap includes an outermost layer comprising a photocatalytic titanium dioxide solution. The liquid titanium dioxide solution, when cured onto the film or laminate, forms a coating that provides a photocatalytic effect when exposed to sunlight and air. Accordingly, the vehicle wrap oxidizes volatile organic compounds (VOCs) and other harmful pollutants at the ground-level. The vehicle wrap may cover all or only a portion of the vehicle.

Figure 1:
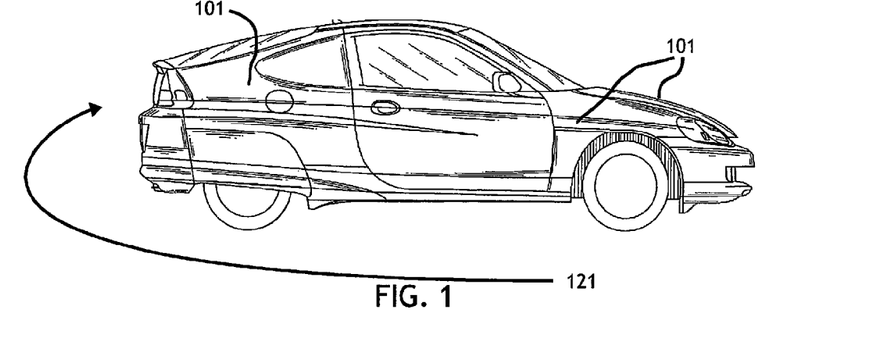
FIG. 1 illustrates a side-view of a vehicle having a photocatalytic air purification vehicle wrap according to the principles of the present invention.

Referring now to FIG. 1, a vehicle 121 including an air purification device 101 is shown according to one preferred and non-limiting embodiment. The air purification device 101 in this example is a vehicle wrap 101 that covers a substantial portion of the vehicle 121. The vehicle wrap 101 comprises a material, such as a thin vinyl, film, laminate, and/or the like, and an outermost layer having photocatalytic and/or hydrophilic properties. As already explained, the outermost layer may include, but is not limited to, titanium dioxide. Although the photocatalytic and/or hydrophilic material may be applied in numerous ways, in a preferred and non-limiting embodiment a liquid solution of titanium dioxide is applied to the film or laminate material.

The vehicle wrap, in non-limiting embodiments, may include one or more graphics, designs, colors, and/or the like, that are applied or printed onto the vehicle wrap (e.g., film or laminate) before or after the titanium dioxide coating is applied. In some non-limiting examples, the graphics, designs, colors, and/or other features may include titanium dioxide (e.g., in the ink or otherwise) and be an outermost layer, or be beneath a transparent or translucent outermost layer of the titanium dioxide coating. Various other arrangements are possible.

In a preferred and non-limiting embodiment, the film or laminate material may comprise, but is not limited to, cast vinyl, calendared vinyl, PVC, polycarbonate, polyethylene terephthalate (PET), polypropolene, aluminum or other thin metallic mediums, and/or any other suitable type of polymer, vinyl, or other like material.

In addition to having oxidation properties, the titanium dioxide coating will provide the vehicle wrap with superhydrophilic self-cleaning properties. Thus, the vehicle wrap (and therefore the vehicle) will stay clean with the combination of sunlight and rain. Moreover, it will be appreciated that other materials having hydrophilic properties may be used on or with the vehicle wrap.

In non-limiting embodiments, the liquid titanium dioxide solution includes titanium dioxide, a wetting agent, and an adhesive. Wetting agent and adhesive additives help coat hydrophobic film or laminate being used for the vehicle wrap. For example, a surfactant may be used as a wetting agent to help evenly distribute the solution over a hydrophobic film or laminate, and a polyurethane may be used as an adhesive to help adhere the solution to the film or laminate. In a preferred but non-limiting embodiment, more than 1 percent but less than 10 percent of the liquid solution is surfactant, and more than 1 percent but less than 10 percent of the liquid solution is polyurethane. In a further preferred and non-limiting embodiment, approximately 2 percent, or a range between 1 and 3 percent, of surfactant is used, and the same or similar percentage or ratio of polyurethane is used. However, it will be appreciated that various ratios may be used depending on the type and properties of film or laminate.

Once the titanium dioxide solution is applied to a surface of the film or laminate, it may be processed by an ultraviolet curing apparatus (e.g., an apparatus or system to expose the material to ultraviolet light/radiation). The UV curing apparatus may be part of a coating apparatus that applies the titanium dioxide solution to the film or laminate as it is fed through rollers of the apparatus. After being applied, the coated film or laminate may then be exposed to the UV radiation to cure the coating. This UV coating process not only dries and cures the liquid application of titanium dioxide, but may also make the vehicle wrap brighter, more brilliant, and add protection against fading and friction.

According to one non-limiting embodiment of the present invention, the film or laminate used for the vehicle wrap may be too thin and/or unsturdy to feed through the coating apparatus. In these circumstances, a rigid medium may be used to feed the film or laminate through the apparatus. The material may first be mounted onto the rigid medium via an adhesive, tacks, clips, or other like devices, and then fed through the coating machine. It will be appreciated that, in some embodiments, the material may be mounted on the rigid medium without any device or apparatus.

It will be appreciated that the photocatalytic materials of the present invention may also be used for other purposes. For example, a film or laminate coated with the titanium dioxide solution and cured may be applied to billboards, floor coverings and floor graphics, road signs, windows, and/or walls. Billboards and road signs may particularly benefit from the present invention due to their proximity to roadways and, therefore, pollutants. The billboards and road signs having been coated in a titanium dioxide solution, or overlaid with a film or laminate having a titanium dioxide solution cured thereon, will self-clean when it rains and will oxidize harmful pollutants. As an example, a road sign may be fed through a coating machine and cured with ultraviolet light after being coated with a liquid titanium dioxide solution. Alternatively, a spray, film or laminate may be applied to existing road signs and/or billboards.

In a further non-limiting embodiment, an air purification device 101 covers a portion of a vehicle and includes a flexible magnetic material adapted to be affixed or otherwise removably adhered to an exterior surface of an automobile or other type of vehicle. The flexible magnetic material in this example includes a photocatalyst, such as titanium dioxide. As described elsewhere, the titanium dioxide solution may be applied to the flexible magnetic material as a liquid coating. However, it will be appreciated that other methods may be used to provide the air purification device 101 with an outermost layer having photocatalytic properties.

In one non-limiting embodiment, a liquid solution of or material containing titanium dioxide is applied to and/or otherwise coated on the magnetic material. However, it will be appreciated that the titanium dioxide or other photocatalytic materials may be introduced to the magnetic material in any number of ways. For example, the titanium dioxide may be applied to a film or laminate, and the film or laminate may be applied to the magnetic material. In other examples, the titanium dioxide may be applied directly to the magnetic material by spraying, dipping, or otherwise coating the magnetic material with a liquid solution or powdered compound of titanium dioxide. It will be appreciated that the magnetic material may be any flexible material such as vinyl, rubber, textiles, etc., that is provided with magnetic properties. For example, the magnetic material may be a preformed sheet-type magnet made of vinyl with a magnetic surface (e.g., the contact surface), and may also be a non-magnetic material that is provided with one or more magnets, or otherwise provided with a magnetic surface.

Figure 4A:
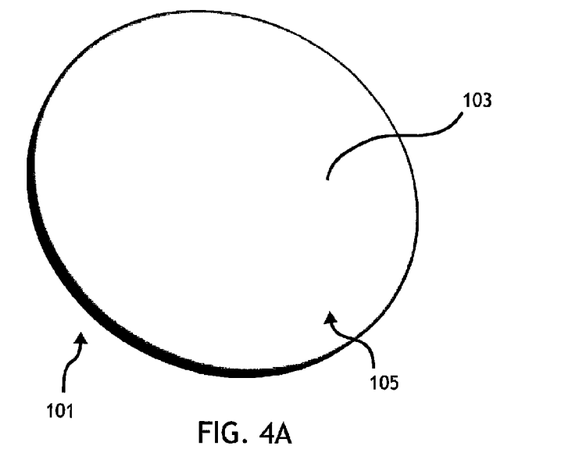
FIG. 4A illustrates a top perspective-view of an embodiment of a photocatalytic air purification device according to the principles of the present invention.
Figure 4B:
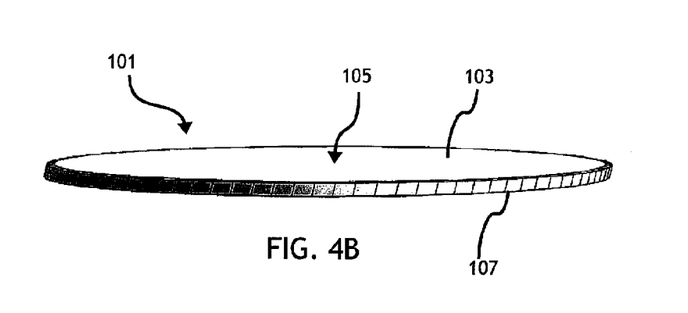
FIG. 4B illustrates a side perspective-view of the embodiment of a photocatalytic air purification device shown in FIG. 4A.
Figure 4C:
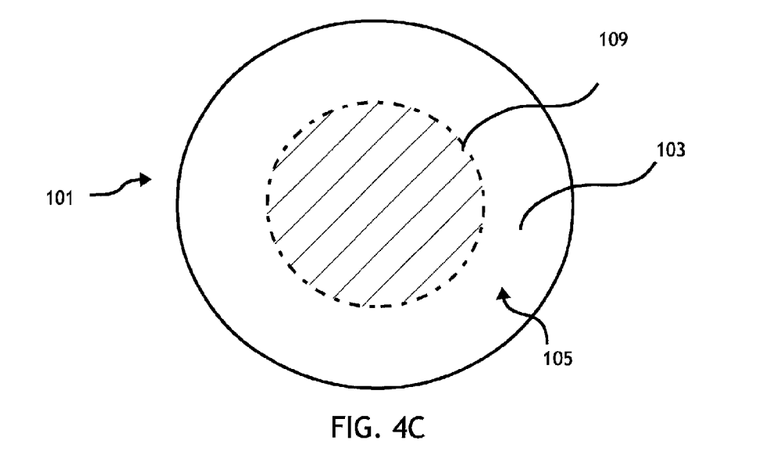
FIG. 4C illustrates a top-view of an embodiment of a photocatalytic air purification device including a graphic.

Referring now to FIGS. 4A, 4B, and 4C, an air purification device 101 is shown according to a non-limiting embodiment. The air purification device 101 in the depicted embodiment is substantially flat and circular, although various shapes and forms may be used. An exposed surface (e.g., outer surface) 103 of the device 101 comprises a photocatalytic material 105, such as titanium dioxide. A contact (e.g., magnetic, static, adhesive, or the like) surface 107 of the device 101 is the surface (side) of the device 101 that adheres to a metallic or plastic surface of a vehicle. When the air purification device 101 is placed onto the exterior of a vehicle, the exposed surface 103 is exposed to the air and ultraviolet (UV) light, allowing the photocatalytic material to oxidize harmful particles including, for example, VOCs.

Referring specifically to FIG. 4C, the air purification device 101 is shown with a graphic 109. The graphic 109 may be applied on top of a vinyl laminate, as an example, by any number of methods or means. In some examples, the graphic 109 may be applied to the magnetic material by directly printing on the air purification device 101 before or after the device 101 is provided with titanium dioxide. The graphic 109 may be silkscreened, embossed, adhered to, or otherwise printed on the air purification device 101. In a preferred but non-limiting embodiment, the air purification device 101 is manufactured by printing or applying a graphic 109 to the exposed surface 103 of the air purification device 101, and then applying titanium dioxide or other photocatalytic materials to the exposed surface 103 on top of the graphic 109. In some examples, prior to the application of the titanium dioxide, a clear or translucent overlaminate or film may be used to cover the exposed surface 103 and graphic 109 and, then, the titanium dioxide may be applied on top of that overlaminate or film. However, it will be appreciated that the titanium dioxide, the graphic 109, and/or any other elements or coatings may be applied to the magnetic material in any number of ways and/or sequences.

In one preferred and non-limiting embodiment, the air purification device 101, as either a full or partial vehicle wrap or a flexible magnetic material, is placed on or otherwise applied to the exterior of a vehicle. The magnetic properties of the air purification device 101 allow it to be removably attached to the exterior of a vehicle such that it can be easily removed and reattached. Further, the air purification device 101 may be fabricated from a flexible and/or pliable material, such that the air purification device 101 can be rolled up and stored conveniently, and form to an uneven surface of an automobile.

Figure 2A:
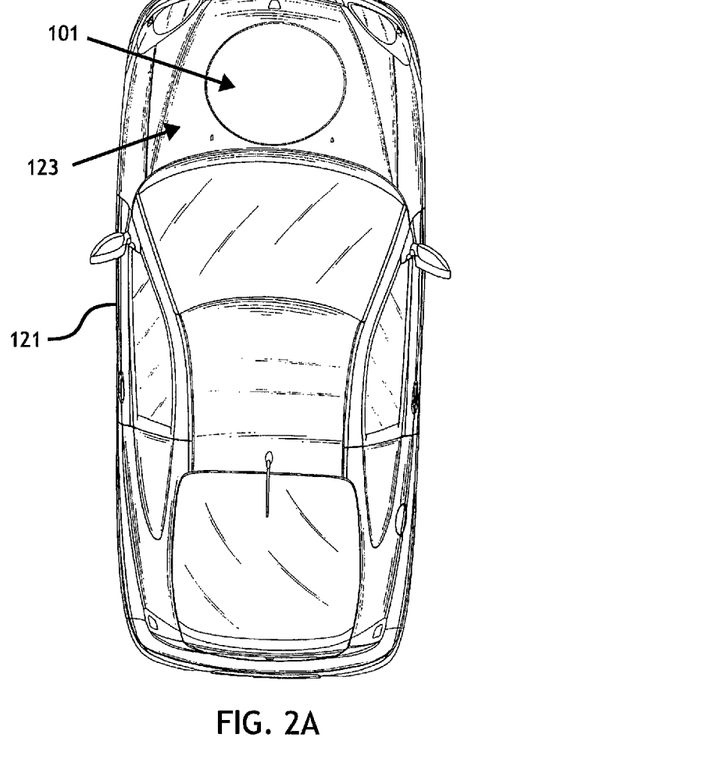
FIG. 2A illustrates a top-view of a vehicle having a photocatalytic air purification device according to the principles of the present invention.
Figure 2B:
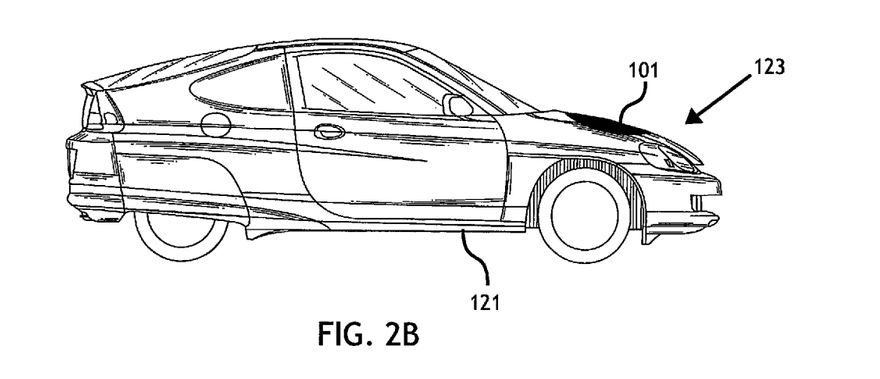
FIG. 2B illustrates a side-view of a vehicle having a photocatalytic air purification device according to the principles of the present invention.

Referring now to FIGS. 2A and 2B, a vehicle 121 is shown with an air purification device 101 according to a non-limiting embodiment. The air purification device 101 is on the front hood 123 of the vehicle 121 and is removably attached to the front hood 123 by means of the magnetic material of the device 101. It will be appreciated that, in some embodiments, the air purification device may also be attached to the front hood 123 or other portion of the vehicle 121 by any number of means such as, for example, static, adhesives, and/or any other attachment mechanisms, arrangements, devices, or methods.

Positioning the air purification device 101 on the front hood 123 of the vehicle 121, as either a flexible magnet or a full or partial vehicle wrap, may provide for the oxidation of some particles exhausted from a leading vehicle (e.g., a vehicle in front of the vehicle 121 having the air purification device 101). Thus, in traffic, the exhaust fumes of the leading vehicle may draft over the front hood of the vehicle 121 behind it and pass over the air purification device 101. The air purification device 101 may also oxidize particles emanating from the hood of the vehicle 121 or elsewhere. Further, the front hood 123 of a vehicle often has a large surface area that can be partially covered with an air purification device 101, and is situated so as to allow ample amounts of UV light from the sun to react with the titanium dioxide. The air purification device 101 may also be placed on the side, top, or back of a vehicle, as examples, or substantially all around the vehicle as a wrap.

A method according to a non-limiting embodiment includes the steps of providing an air purification device 101, and applying the air purification device 101 to an exterior surface of a vehicle 121 such as, but not limited to, a front hood 123 of the vehicle 121. In another example, a method for making an air purification device 101 includes providing a magnetic material and coating that material with titanium dioxide.

Figure 3A:
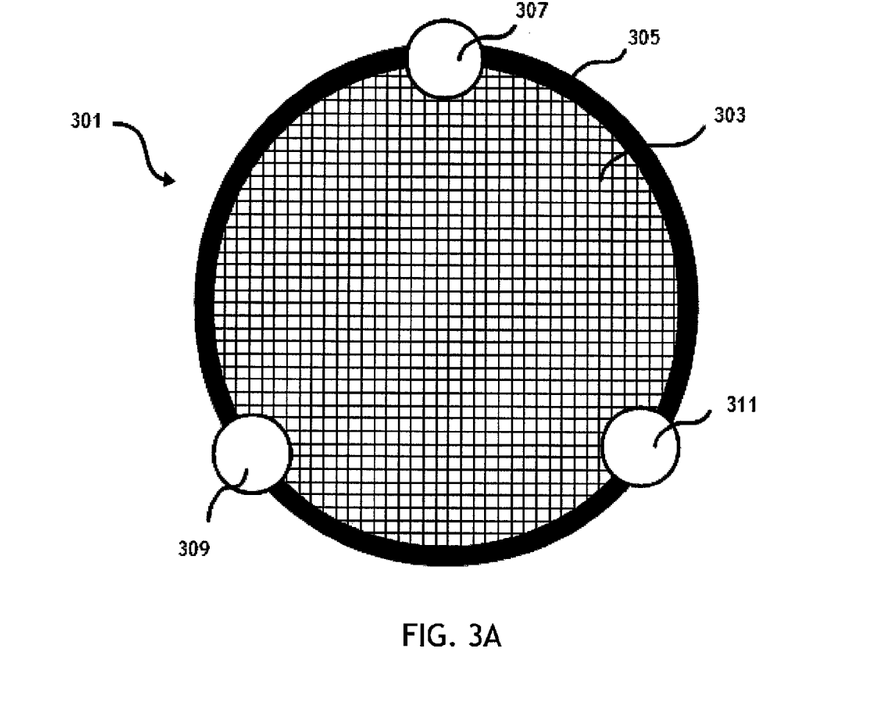
FIG. 3A illustrates a top-view of a photocatalytic air purification device according to the principles of the present invention.
Figure 3B:
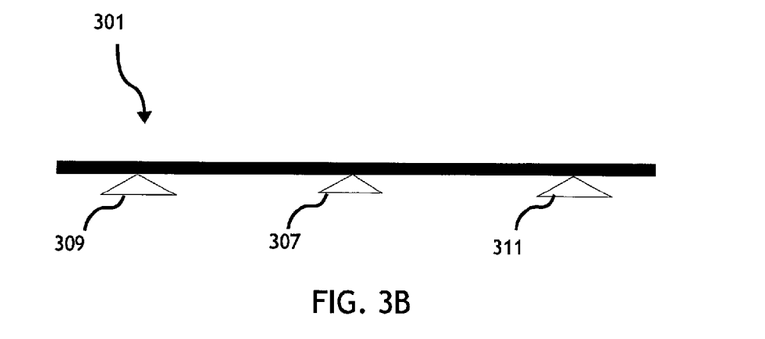
FIG. 3B illustrates a side-view of a photocatalytic air purification device according to the principles of the present invention.

Referring now to FIGS. 3A and 3B, an air purification device 301 is shown according to a further non-limiting embodiment. FIG. 3A depicts a top-view of the air purification device 301 and FIG. 3B depicts a side-view of the air purification device 301. The air purification device 301 shown includes a substantially flat and circular screen 303, a rim 305 surrounding the screen 303, and attachment means 307, 309, 311 spaced evenly around the rim 305.

With continued reference to FIGS. 3A and 3B, the attachment means 307, 309, 311 may include one or more suction cups, hooks, magnets, adhesives, and/or fittings. In the embodiment depicted, the attachment means 307, 309, 311 include suction cups adapted to be attached to a window or other smooth surface. However, it will be appreciated that any number of attachment means may be used, and that the attachment means may include any structure, assembly, or device that removably attaches the air purification device 301 to a surface.

In a further non-limiting embodiment, a clear or translucent film, such as an overlaminate, may be provided with titanium dioxide and used to cover the air purification device 101. In this example embodiment, the film may be used to protect a graphic 109 that is on the device 101, or to simply and efficiently provide a device 101 with the necessary titanium dioxide as an outermost layer to produce photocatalytic effects.

Figure 5:
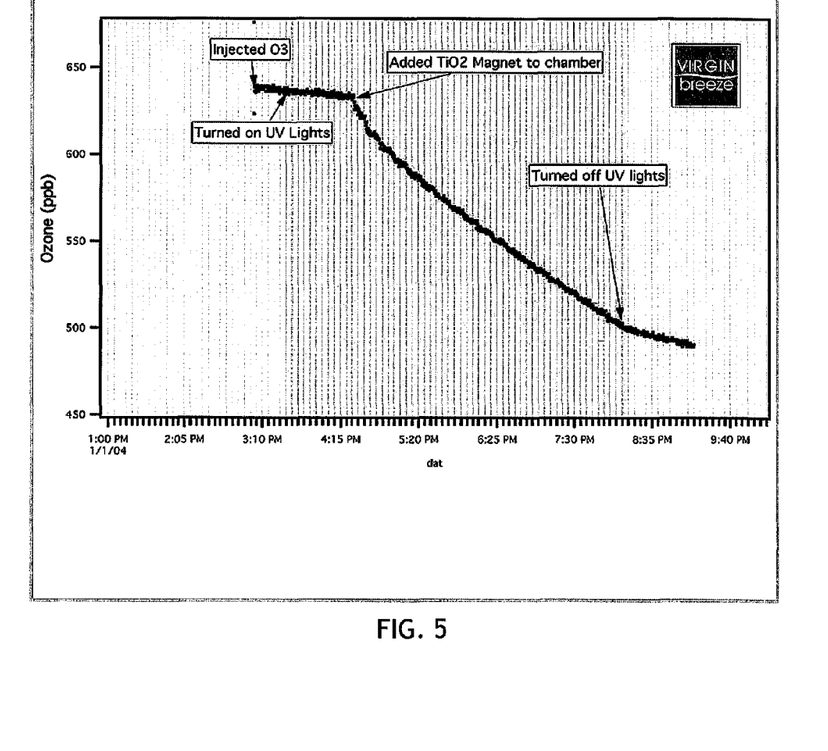
FIG. 5 illustrates a chart showing the reduction of ozone over time by using a photocatalytic air purification device.

Referring now to FIG. 5, a chart is shown depicting the benefits of one non-limiting embodiment of the present invention. This chart was generated by testing an embodiment of the present invention in a smog chamber. As can be seen, ozone was injected into the chamber. Subsequently, UV lights were turned on in the chamber and the air purification device was applied. As can be seen, the ozone levels dropped approximately 150 ppb after application of the present invention in combination with UV light. It will be appreciated that the results shown in FIG. 5 are merely exemplary, and that results may differ depending upon the surface area covered by titanium dioxide, the size of the testing facility, the intensity of the UV light, and other variables.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A vehicle wrap for at least partially covering an exterior surface of a vehicle, comprising:
   a film or laminate material comprising a first surface area and a second surface area, the first surface area adapted to adhere to the exterior surface of the vehicle; and
   a coating layer disposed on the second surface, the coating layer comprising a titanium dioxide solution cured onto the film or laminate material, the titanium dioxide solution comprising liquid titanium dioxide, at least one surfactant substance, and at least one adhesive, and wherein the coating layer is an outermost layer of the vehicle wrap such that the cured titanium dioxide solution is exposed to air surrounding the vehicle when the first surface area is adhered to the exterior surface of the vehicle.

2. The vehicle wrap of claim 1, wherein the at least one surfactant substance comprises at least 1 percent of the titanium dioxide solution.

3. The vehicle wrap of claim 2, wherein the at least one surfactant substance is less than 5 percent of the titanium dioxide solution.

4. The vehicle wrap of claim 1, wherein the at least one adhesive comprises polyurethane, and wherein the polyurethane comprises at least 1 percent of the titanium dioxide solution.

5. The vehicle wrap of claim 1, wherein the at least one adhesive comprises polyurethane, and wherein the polyurethane is less than 5 percent of the titanium dioxide solution.

6. The vehicle wrap of claim 1, wherein the film or laminate material comprises at least one of the following: cast vinyl, calendared vinyl, PVC, polycarbonate, polyethylene terephthalate (PET), or polypropolene.

7. The vehicle wrap of claim 1, wherein the first surface comprises a magnetic material adapted to magnetically adhere to the exterior of the vehicle, and wherein the film or laminate material comprises at least one graphic beneath the coating layer.

8. A method for making a vehicle wrap, comprising:
   providing a material comprising a first surface and a second surface opposite the first surface, the first surface adapted to adhere to an exterior surface of a vehicle;
   printing at least one graphic or image on the second surface of the material;
   coating the second surface of the material with a liquid titanium dioxide solution using a coating machine, the liquid titanium dioxide solution comprising at least one surfactant substance, at least one adhesive, and titanium dioxide; and
   curing the coated material with ultraviolet radiation.

9. The method of claim 8, wherein coating the second surface of the material with the liquid titanium dioxide solution further comprises:
   mounting the material on a rigid medium;
   feeding the material and rigid medium into the coating machine; and
   removing the material from the rigid medium.

10. The method of claim 8, wherein the at least one adhesive comprises polyurethane.

11. The method of claim 8, wherein the at least one surfactant is at least 1 percent and less than 5 percent of the liquid titanium dioxide solution.

12. The method of claim 8, wherein the at least one adhesive is at least 1 percent and less than 5 percent of the liquid titanium dioxide solution.

13. The method of claim 8, wherein the material comprises an overlaminate medium.

14. The vehicle wrap of claim 1, wherein the titanium dioxide solution is cured onto the film or laminate material with ultraviolet radiation.

15. A photocatalytic material for covering a surface or object, comprising a first surface area and a second surface area opposite the first surface area, the first surface area adapted to removably adhere to the surface or object, the second surface area comprising a coating of a titanium dioxide solution that has been cured, the titanium dioxide solution comprising at least one surfactant, at least one adhesive, and liquid titanium dioxide, wherein the coating on the second surface area is the outermost layer of the material and is exposed to air when the first surface area of the material is adhered to the surface or object such that the coating produces a photocatalytic effect when the second surface area is exposed to air and light.

16. The photocatalytic material of claim 15, wherein the at least one adhesive comprises polyurethane.

17. The photocatalytic material of claim 15, wherein the at least one surfactant substance comprises between 1 percent and 5 percent of the titanium dioxide solution, and wherein the at least one adhesive comprises between 1 percent and 5 percent of the titanium dioxide solution.

18. The photocatalytic material of claim 15, wherein the material comprises at least one of the following: cast vinyl, calendared vinyl, PVC, polycarbonate, polyethylene terephthalate (PET), or polypropolene.

19. The photocatalytic material of claim 15, wherein the first surface area comprises a magnetic material adapted to magnetically adhere to the surface or object.

20. The photocatalytic material of claim 15, wherein the second surface area comprises at least one printed graphic or image beneath the coating.

* * * * *